US010076938B2

(12) United States Patent
Olmedo et al.

(10) Patent No.: US 10,076,938 B2
(45) Date of Patent: Sep. 18, 2018

(54) ALL-TERRAIN VEHICLE

(71) Applicant: Copperstone Technologies Ltd., Calgary (CA)

(72) Inventors: Nicolas Olmedo, Edmonton (CA); Stephen Dwyer, High River (CA); Michael Lipsett, Spruce Grove (CA); James Yuen, Calgary (CA)

(73) Assignee: Copperstone Technologies Ltd., Calgary (CA)

( * ) Notice: Subject to any disclaimer, the term of this patent is extended or adjusted under 35 U.S.C. 154(b) by 248 days.

(21) Appl. No.: 15/063,846

(22) Filed: Mar. 8, 2016

(65) Prior Publication Data
US 2017/0259633 A1    Sep. 14, 2017

(51) Int. Cl.
| | |
|---|---|
| *B60F 3/00* | (2006.01) |
| *E21B 25/00* | (2006.01) |
| *G01N 33/24* | (2006.01) |
| *G01N 3/42* | (2006.01) |

(52) U.S. Cl.
CPC .......... *B60F 3/0023* (2013.01); *B60F 3/0061* (2013.01); *E21B 25/005* (2013.01); *G01N 3/42* (2013.01); *G01N 33/24* (2013.01)

(58) Field of Classification Search
CPC .... B60F 3/0023; B60F 3/0061; E21B 25/005; G01N 3/42; G01N 33/24
See application file for complete search history.

(56) References Cited

U.S. PATENT DOCUMENTS

| | | | | |
|---|---|---|---|---|
| 2,376,647 | A * | 5/1945 | Akins | B60F 3/0023 440/12.53 |
| 2,764,117 | A * | 9/1956 | De Persia | B60F 3/0023 125/13.03 |
| 3,250,239 | A * | 5/1966 | Chico Garate | B60F 3/0023 440/12.65 |
| 3,266,588 | A * | 8/1966 | Neumeyer | B60F 3/0023 180/6.2 |
| 3,333,563 | A * | 8/1967 | De Bakker | B60F 3/0023 440/12.65 |
| 3,354,861 | A * | 11/1967 | Wilcox | B60F 3/0023 440/12.65 |
| 3,376,945 | A * | 4/1968 | Kaprelian | B60F 3/0023 180/14.1 |

(Continued)

FOREIGN PATENT DOCUMENTS

| | | | | |
|---|---|---|---|---|
| DE | | 3524616 A1 * | 1/1987 | B60F 3/0061 |
| WO | WO 2012162750 A1 * | | 12/2012 | B63H 1/12 |

OTHER PUBLICATIONS

Machine translation of DE 3524616.*

*Primary Examiner* — David Bolduc
(74) *Attorney, Agent, or Firm* — Mu P.C.

(57) ABSTRACT

An all-terrain rover has a ladder frame having one or more crosspieces, two drive units connected on opposite sides of the frame, first and second auger cylinders engaged with the drive. The drive units are in contact with the axes of the auger cylinders and the flange of the first cylinder is wound in an opposite direction to the flange of the second cylinder. The cylinders are counter-rotated to urge the rover forward. Sampling equipment is mounted on the frame. In an embodiment, each cylinder further comprises a conical end cap at each end. Each cylinder may have a frustaconical end cap at each end, and each cylinder may be buoyant.

16 Claims, 7 Drawing Sheets

(56) References Cited

U.S. PATENT DOCUMENTS

| | | | | |
|---|---|---|---|---|
| 3,381,650 A * | 5/1968 | Itoh | B60F 3/0023 | 416/84 |
| 3,395,671 A * | 8/1968 | Zimmerman, Jr. | B60F 3/0023 | 180/6.44 |
| 3,396,690 A * | 8/1968 | Tsunazawa | B62D 57/02 | 180/6.2 |
| 3,682,127 A * | 8/1972 | Waquet | B60F 3/0023 | 440/12.65 |
| 3,746,112 A * | 7/1973 | Ilon | B60B 19/003 | 180/6.2 |
| 3,970,029 A * | 7/1976 | Bibaut | B60F 3/0038 | 114/61.15 |
| 4,476,948 A * | 10/1984 | Komoto | B60F 3/0023 | 180/7.2 |
| 5,203,274 A * | 4/1993 | Hart | B60F 3/0023 | 114/124 |
| 5,203,729 A * | 4/1993 | Beller | B60F 3/0023 | 440/113 |
| 5,392,871 A * | 2/1995 | McFarland | G05G 9/047 | 114/144 R |
| 5,509,370 A * | 4/1996 | Kovacs | B60F 3/0023 | 180/7.2 |
| 2005/0118903 A1* | 6/2005 | Leonov | A63H 17/26 | 440/98 |
| 2010/0005857 A1* | 1/2010 | Zhang | B63C 11/48 | 73/29.02 |
| 2010/0130077 A1* | 5/2010 | Foo | B60F 3/0023 | 440/12.65 |
| 2012/0184159 A1* | 7/2012 | Fuglsang | B60F 3/0015 | 440/12.63 |
| 2015/0346374 A1* | 12/2015 | Campbell | G01N 27/041 | 324/366 |
| 2016/0114887 A1* | 4/2016 | Zhou | B60F 5/02 | 348/148 |
| 2016/0272291 A1* | 9/2016 | Outa | B60F 3/0015 | |

\* cited by examiner

ALL-TERRAIN VEHICLE

BACKGROUND OF THE INVENTION

1. Field of Invention

The present invention relates to the field of geotechnical sample procurement, and particularly the use of remote-controlled, unmanned vehicles for sampling and measurement in tailings and other difficult terrain.

2. Description of Related Art

Tailings deposits and other mining and oil-producing by-products must be periodically sampled to determine environmental impact, process efficiency, as well as regulatory compliance, but the locations are often remote and terrain is irregular, especially in the North where permafrost may exist or the ground is frozen for large parts of the year. The monitoring requirement means that multiple samples must be taken annually.

Typically, oil sands operators must wait until the deposits freeze over in the winter to be able to move safely across the deposits. Samples may be taken by drilling out cores from a sample space. For winter sampling, a CRREL barrel sampler may be used, which was developed to collect a core of frozen soil or ice in a permafrost zones. The soil core can be sent to the laboratory for characterizing the fines content. The resulting core hole can then be used to further sample the unfrozen deposit below or measure other properties such as strength by using cone penetrometer testing (CPT) or vane shear testing (VST).

For tailings ponds, the top surface sample location should be shielded from waves, and variability due to boat wake etc. should be considered. The top of pond survey needs to be concurrent with the sampling program to provide accuracy in the measurement as the pond elevation may vary throughout the program. The midline interface is the boundary between the water and the top of the underlying fluid fine tailings. The mudline interface can be measured using a 200 kHz sonar or a density plate. The sonar uses a sound pulse directed downwardly to detect the mudline, and the time of travel is measured. The density plate involves a thin plate with weights, wherein the plate is allowed to sink and where it stops is the mud line interface. The fluid fine tailings overlying the bottom of the pond are also sampled using a drop sounding tool that measures the depth and corrects for inclination, a cone penetration test, or a combination of these tests is used. However, on fine grained thin-lift deposits (e.g. centrifuge cake, dMFT/TRO, AFD, NST) the tailings are too thick for traditional methods, and yet not strong enough to support people or equipment. These ponds can only be sampled by large amphibious barge in the summer or from the frozen surface in the winter. This prevents annual monitoring and trend analysis that more frequent sampling would permit. However, the deposits are practically inaccessible in the summer. In other areas, samples are in a fluid form but are typically hazardous for a human operator. Additionally, access is by a number of different possible terrains and there is no easy access to the water, for example, without endangering an operator.

Many other mining operations worldwide also produce fluid tailings with limited access, which present challenges to monitor. Work in other fields like marsh and wetlands, ice and thin ice are also limited by physical access constraints.

Based on the foregoing, there is a need in the art for a remote all-terrain rover that may be deployed and access tailings and other areas of interest over a number of different terrain and climate types, including ice and permafrost, snow, mud, marsh and wetlands, carrying sampling tools, instruments, and manipulators.

SUMMARY OF THE INVENTION

An all-terrain rover has a ladder frame having one or more crosspieces, two drive units connected on opposite sides of the frame, first and second auger cylinders engaged with the drive units so as to be urged into rotation by the drive units, each cylinder comprising a sealed hollow cylinder; and a spiral auger flange affixed to the exterior of the cylinder, wherein the drive units are in contact with the axes of the auger cylinders are parallel and the flange of the first cylinder is wound in an opposite direction to the flange of the second cylinder, and wherein the cylinders are each counter-rotated to urge the rover forward.

In one embodiment sampling equipment is mounted on the frame. In another, each cylinder further comprises a conical end cap at each end. Each cylinder may have a frustaconical end cap at each end, and each cylinder may be buoyant. Each cylinder may be coated with a coating selected from the group consisting of Teflon, "never wet", lard, vegetable oil, or other antifouling coating.

A brush or other cleaning unit may be mounted adjacent to each of the cylinders to clean the surface as the cylinder rotates. Each cylinder may be rotated in the same direction to urge the rover in a sideways direction. A single cylinder can be rotated to produce a skid turn, or multiple cylinders can be rotated at differential speeds to turn the rover.

A control unit may be connected to each of the drive units to control a rotation speed and direction of the drive units, and the rover may be controlled in a remote-controlled configuration or in a robotic configuration.

In an embodiment, the all-terrain rover has third and fourth cylinders, wherein the third cylinder is adjacent and coaxial to the first cylinder, and the fourth cylinder is adjacent and coaxial to the second cylinder.

The all-terrain rover may have a platform across the frame. The sampling equipment comprises a valved core sampler tip connected to a descent mechanism to lower the tip into a surface below the rover. The sampling equipment may have a cone penetrometer connected to a descent mechanism to lower the tip into a surface below the rover. An excavator arm may be attached to the frame.

The foregoing, and other features and advantages of the invention, will be apparent from the following, more particular description of the preferred embodiments of the invention, the accompanying drawings, and the claims.

BRIEF DESCRIPTION OF THE DRAWINGS

For a more complete understanding of the present invention, the objects and advantages thereof, reference is now made to the ensuing descriptions taken in connection with the accompanying drawings briefly described as follows.

DETAILED DESCRIPTION OF THE INVENTION

Figure 1:
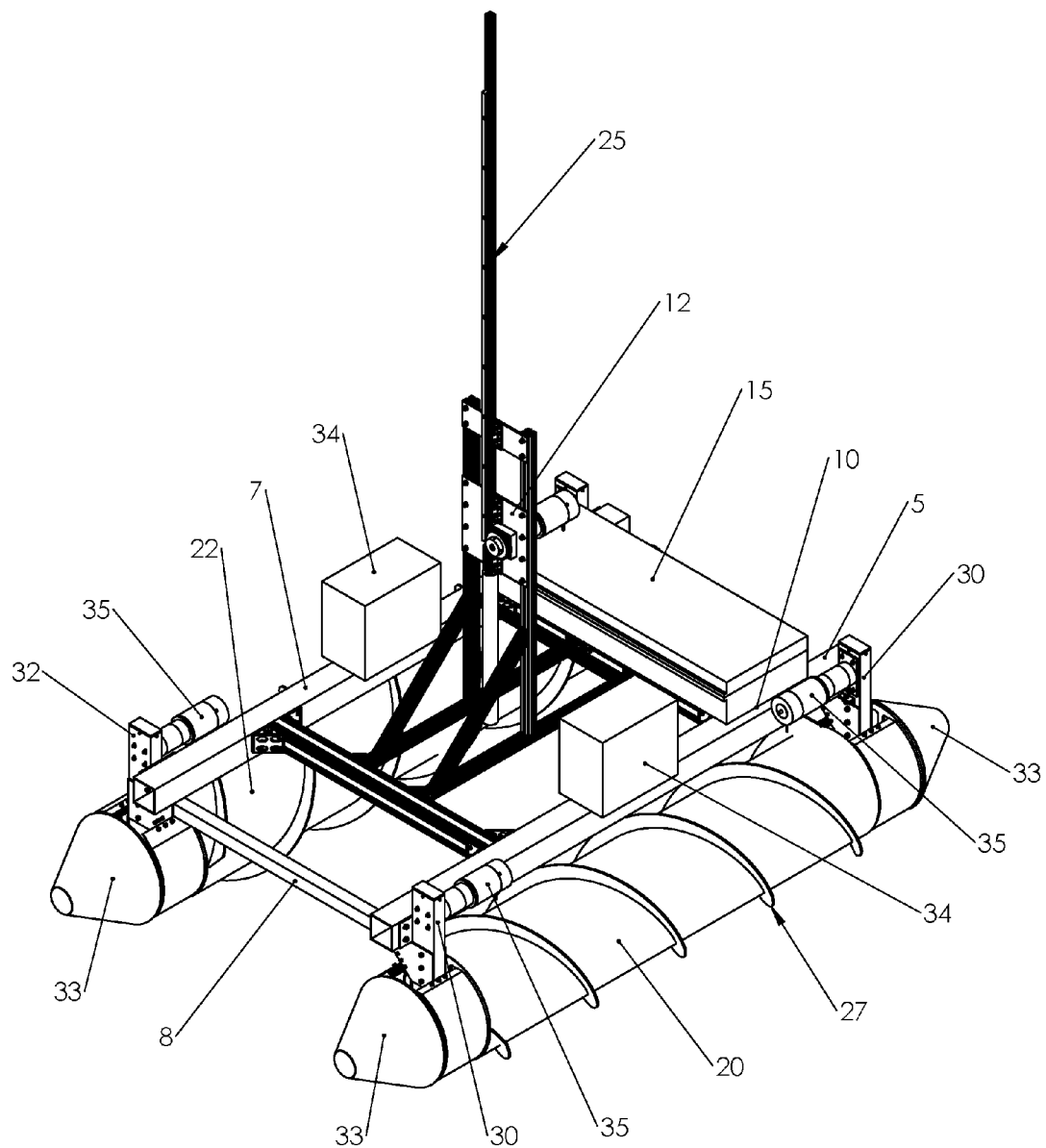
FIG. 1 is a perspective view of the all-terrain rover, according to an embodiment of the present invention.
Figure 2:
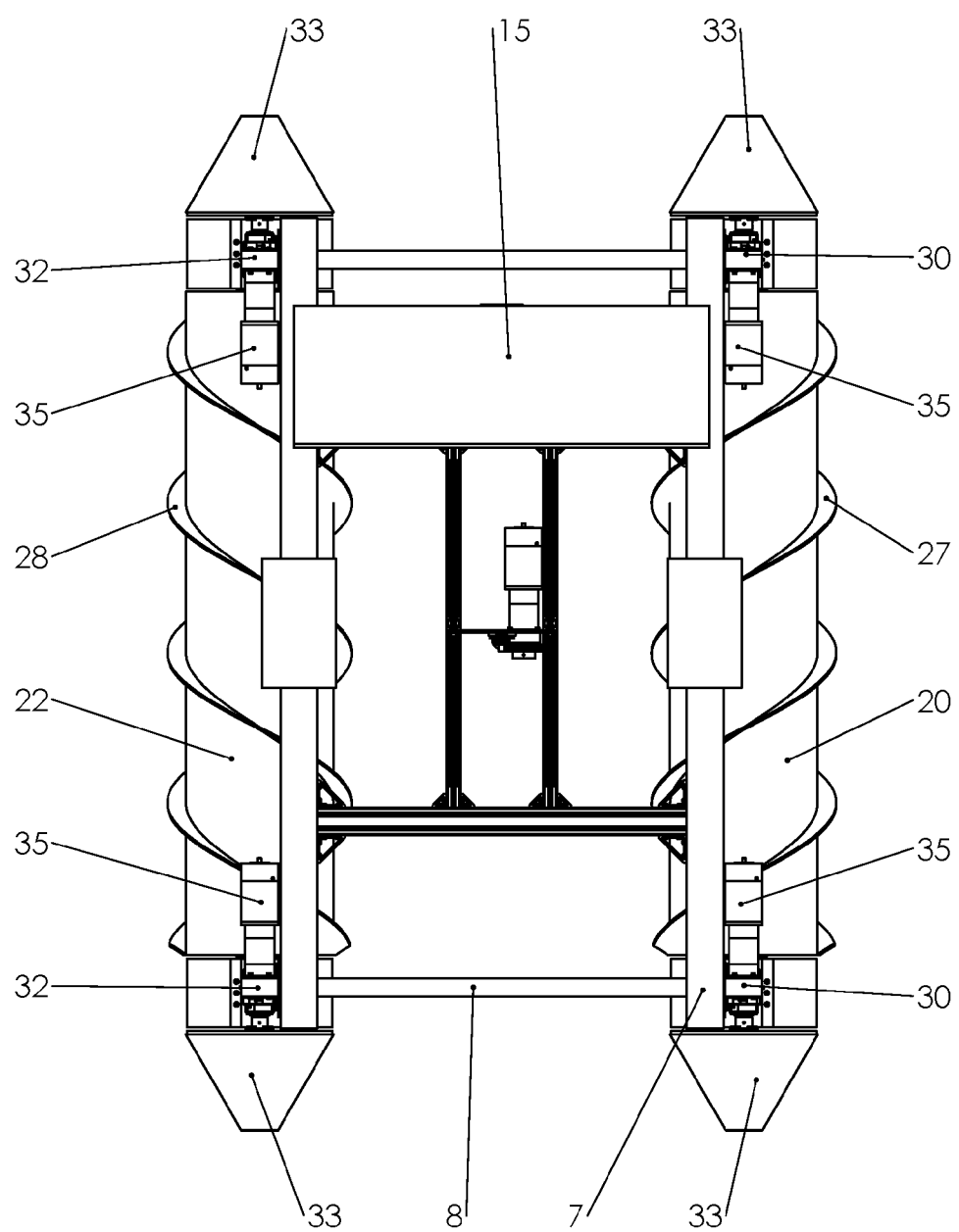
FIG. 2 is a top plan view of the all-terrain rover, according to an embodiment of the present invention.
Figure 3:
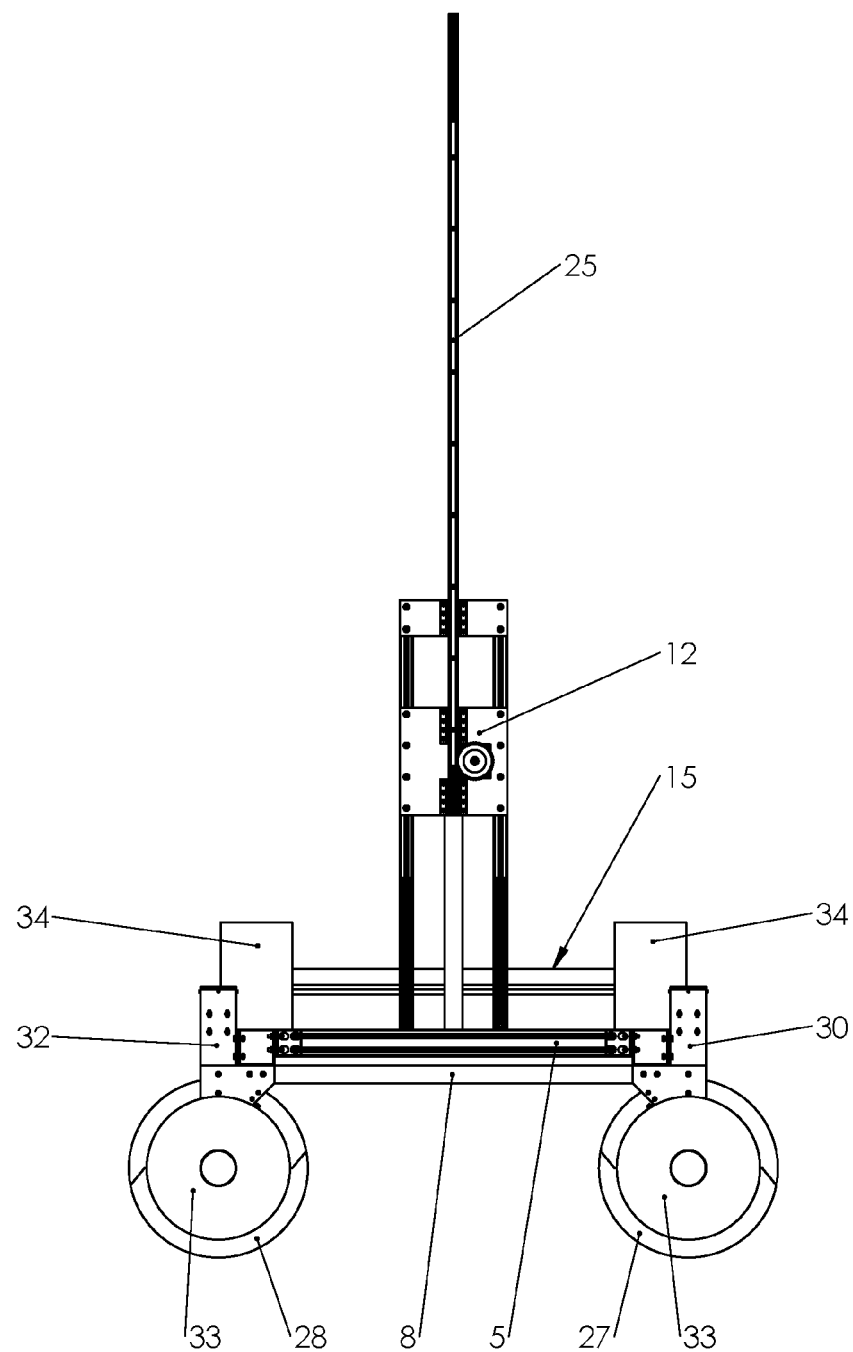
FIG. 3 is a front elevation view of the all-terrain rover, according to an embodiment of the present invention.
Figure 4:
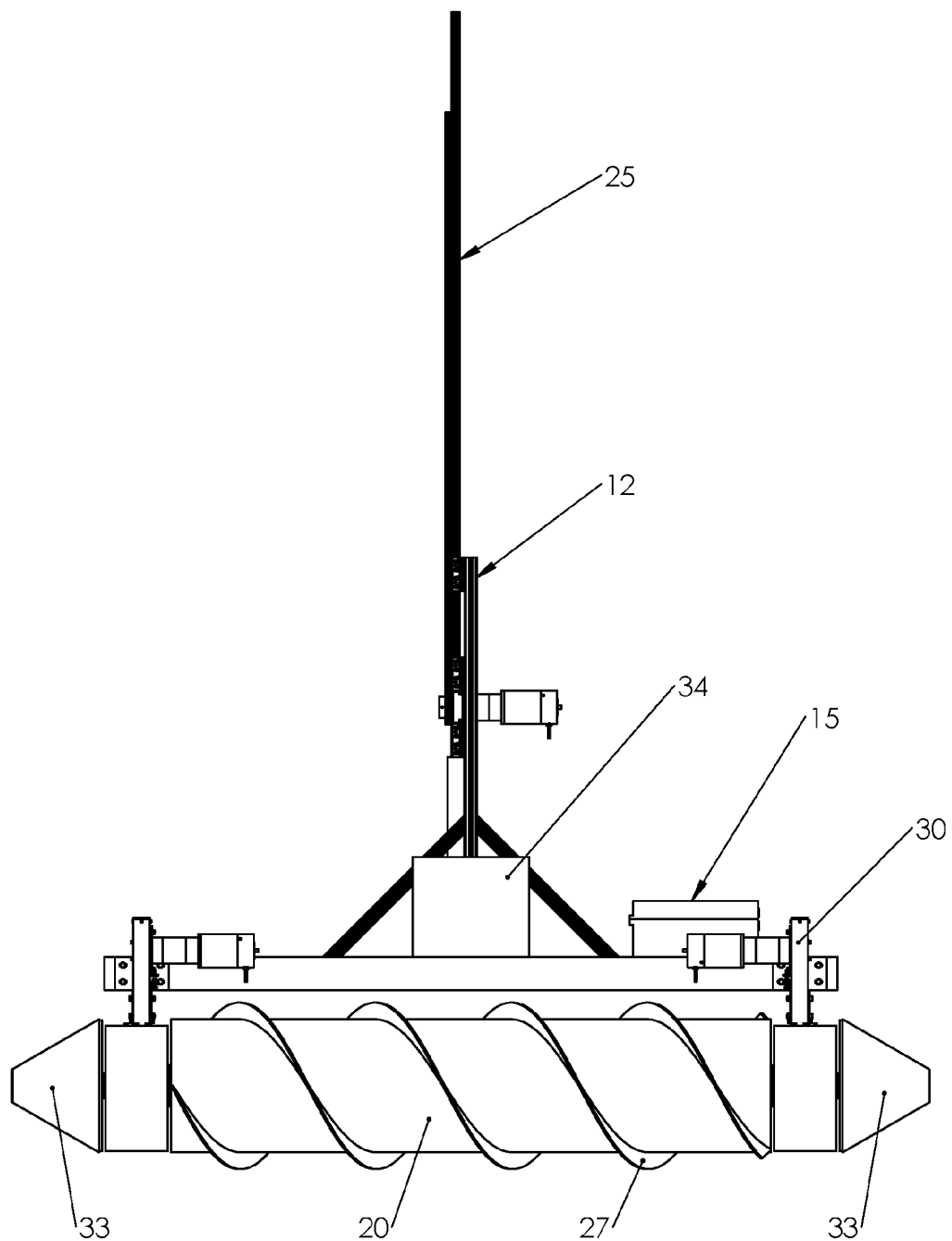
FIG. 4 is a side elevation view of the all-terrain rover, according to an embodiment of the present invention.

Preferred embodiments of the present invention and their advantages may be understood by referring to FIGS. 1-8, wherein like reference numerals refer to like elements.

The all-terrain rover may be remote-controlled or robot-controlled (autonomously-controlled), and is capable of maneuvering by screw-propulsion over a variety of terrain, from hard ground, to soft and sticky tailings deposits, to water and marshes, while carrying payloads to collect samples and make geotechnical measurements at the surface and below the surface. In one embodiment the system is unmanned, and has autonomous operation capability such that it may drive over tailings deposits that are currently inaccessible to other vehicles, or drive submerged. Of particular interest are the oil sands Mature Fine Tailings (MFT) and centrifuge output deposits. The immediate problem it solves is year-round access to certain types of tailings deposits for sample collection and monitoring. This will allow the operators to monitor the performance of their tailings processing at any time, instead of needing to wait until the deposits freeze over in the winter. There are also many other mining operations worldwide producing fluid tailings that may be monitored by the rover.

With reference to FIGS. 1-4, the rover has a ladder frame 5 that consists generally of edge beams 7 connected by one or more crosspieces 8. Mounted to one or more crosspieces 8 is a platform 10 having payload systems 12 and utility box (containing control/electronics/electrical systems) 15 containing equipment/payload affixed thereto, and maintaining a distance between the auger cylinders 20, 22 or rollers that are rotated to provide propulsion. The equipment/payload may be contained within the utility box. The rover may also have sampling equipment 25 mounted on the payload system 12 or elsewhere on the rover, to easily procure a sample when the rover is correctly positioned.

The ladder frame 5 may be a lightweight frame out of aluminum or a steel truss frame, and may include composite materials, or a combination of materials. A fixed frame or an extensible frame allows for easy transport but may be expanded to a larger footprint to improve stability. The frame may protrude completely out of the fluid or the frame may include a floating hull section, in which case a friction-reducing coating may be used, or a friction reducing compound applied periodically by pumping it through ports in the hull to lubricate the hull. The hull may also allow for submerged operation.

The auger cylinders 20, 22 lie along each side of the frame 5 or under the frame 5. At each end of the cylinder 20, the frame 5 is affixed to a drive unit 30, wherein cylinder 20 is suspended between the drive units 30 such that the cylinder 20 is motivated by the drive units 30, 32 to rotate in place along the axis of the cylinder, when so motivated by the cylinder drive. Similarly, drive units 32 are located on either side of cylinder 22 to suspend the cylinder and provide rotational force thereto. In one embodiment, the drive unit 30, 32 is only at one end of the cylinder, and an idler is mounted at the other, such that the cylinder receives drive motivation only at one end. Cylinder 20 has a helical spiral auger flange 27 and cylinder 22 has a spiral flange 28. At each end of the cylinder drive unit is a frustaconical or generally conical end cap 33 that enables the rover to push past or avoid objects it moves into the prevent damage to the drive units 30, 32 and to help maintain floatation and streamline the drive mechanism. In an embodiment the conical ends 33 may have auger flanges to assist in locomotion and breaking ground or ice in the path of the rover. In an embodiment the cylinders 20, 22 may be tapered at each end to include the function of the cones. In an embodiment a hull bow may be added at each end of the cylinders 20, 22 to aid in progress through water and very soft ground. The screw drive provides a preferable buoyancy efficiency (for example 92.5 kg/m) over buoyant track or wheel solutions.

On a matched pair of cylinders, the spiral flanges 27, 28 are oriented opposite to one another (one clockwise, the other counter clockwise) so that when the cylinders are in counter-rotation a forward or reverse motion results with reference to the contact between the flange and the ground. The flange is rigid and wide so as to engage and cut into the surface, to produce a positive grip in the surface (ideally a soft surface). In an embodiment, the flange angle relative to the axis of the cylinder is 30 degrees, with a thread height: cylinder diameter ratio of 0.375. However, as described below, the thread attack angle and height may be varied for better performance on certain surfaces. The cylinders 20, 22 are hollow and sealed in an embodiment, to provide floatation when the vehicle is on a fluid surface, so as to provide amphibious capability. In an embodiment, the cylinders may provide full buoyancy to the rover, and in another embodiment, the cylinders are only partially buoyant to permit the rover to submerge. Cylinder 20, 22 materials may include metal, plastic, rubber, composite materials, or a combination, and may include coatings to improve wear resistance and reduce drag and adhesion, either temporarily applied or permanently bonded to the surface. Example coatings are TEFLON, "Never Wet", lard, or vegetable oil. Alternatively, an active system with air or liquid jets may be used to keep the cylinder surfaces clear, wherein the jets project fluid or air onto the surfaces to remove debris. A brush or movable scraper may be mounted to the frame and in contact with the cylinder 20, 22 surface to scrape or brush off mud or soil adhering to the cylinders as the cylinder rotates.

The drive units 30, 32 comprise an electric motor 35 in positive connection with a cylinder by means of a mechanical transmission. The transmission may include elements for changing its gear ratio while the rover is deployed to improve its capability to handle various terrain types. In one embodiment, there is a chain and sprocket drive between the motors 35 and cylinder 20, 22 shafts. In another embodiment, the motor output is directly connected to the cylinder or connected through a gearbox. The drive units may provide suspension, in suspending the cylinders by springs and shock absorbers. The suspension assists the cylinder to pitch up and down over obstacles as well as some vertical motion, such that the maximum surface area of each cylinder is in contact with the ground at all times. The frame may be articulated to provide further adaptability of the rover over uneven terrain, and to maintain the cylinders in contact with the surface at all times.

The drive units 30, 32 are connected to a power system, which powers the drive units 30, 32 in counter-rotation so that and the flange 27 bites the ground and moves the rover forward or backward, wherein the side-to-side motion of the auger drive cancels out by the counter-rotation. In one embodiment, the power system uses a battery system 34, electrically powering the drive units 30, 32. In another embodiment, the power system provides hydraulic pressure, which powers the drive units 30, 32, which may be connected to the cylinders 20, 22 either directly or through a transmission system.

The control system 15 comprises a microcontroller or processor or computer, along with a wireless transmitter/receiver and antenna. The control system 15 is electrically connected and provides signals to control movement of the rover and the sampling equipment. Further, a GPS unit receives positional feedback and is connected to the microcontroller to provide positional data. In one embodiment, a warning light and emergency stop buttons provide additional user feedback and control. The antenna may be used to transmit and receive data with a base station, control center, or remote controller. The control system may be controlled in a robot configuration or a remote-controlled configuration. No specific changes in rover hardware are required to change between these configurations.

The controller engages in speed control where the ground speed or screw speed is maintained at a desired rate by the onboard controller to achieve a desired locomotion. Speed may be determined by GPS as well. The controller also engages in torque control where the torque on each screw is maintained at a desired level to achieve a desired locomotion. Automated routines are available so that the rover can perform these tasks without direct user input are facilitated through software in the controller. Control routines are uploaded to take into account feedback from the sensors on the rover to facilitate robotic or autonomous control mode, and so the rover can avoid getting stuck, and if it does get stuck, some strategies to free itself are included in the controller.

In a robot configuration, the robot is instructed with a positional and sampling goal. The control system then initiates movement of the rollers to direct the rover to the desired sampling location, and provides signals to actuate the sampling equipment to procure a sample. In this mode no direct control or supervision of the robot is required. The internal controller calculates the drive motor movements required to get the rover to the commanded position. This mode is advantageous when many measurements or samples are required from a certain area, drastically reducing the manpower and operator training required to conduct the work.

In a remote-controlled configuration, an operator provides control signals to the rover to direct the rover to a location, wherein the operator may have visual contact with the rover, and direct according to what he or she sees, or the rover may provide GPS location, orientation and cameras showing the vicinity, such that the operator may determine an appropriate course of action at a given moment based on the input from the rover. In this mode the control signals provided are more directly sent as commands for certain rotations of the drive motors.

The rover has a series of sensors, all connected to the microcontroller. A system of drive sensors comprises sensors to detect the speed and direction of the cylinder rotation, GPS to detect position and motion, climatic sensors to detect temperature humidity and wind speed. Further sensors, including accelerometers, indicate the orientation of the rover to the microcontroller. External cameras including depth sensing cameras may be used to determine terrain in the rover's vicinity to prevent the rover from passing over an embankment, for example. The battery systems monitor the voltage and battery life remaining as well as the output of the battery towards the propulsion systems. Payload sensors detect the position and speed of the payload so that the deployment speed and depth can be accurately controlled.

In order to effect motion of the rover, the cylinders 20, 22 may be rotated in counter-rotation in order to move the rover forward (moving the flange contact point backwards relative to the rover body), or in the reverse counter-rotation to move the rover in reverse. One cylinder may rotate, and the other rest immobile, resulting in a skid turn on some ground types. The auger cylinders may be rotated in the same direction to provide a sideways motion of the vehicle to overcome an obstacle at the front or back, for example. In a submersible embodiment, the rollers provide forward and backward motion through water. For example, the cylinders may be rotated in the same direction, and the rover may climb sideways over smaller obstacles. Rotating cylinders in the same direction can also be used to traverse hard ground and other ground types where the forward screwing motion is difficult or inefficient, but steering is not possible unless the cylinder 20, 22 angles are actuated with respect to the frame 7, 8. In an embodiment, actuators (not shown) are present at one or both sides of the cylinders to angle the cylinder relative to the frame 7, 8.

Figure 5A:
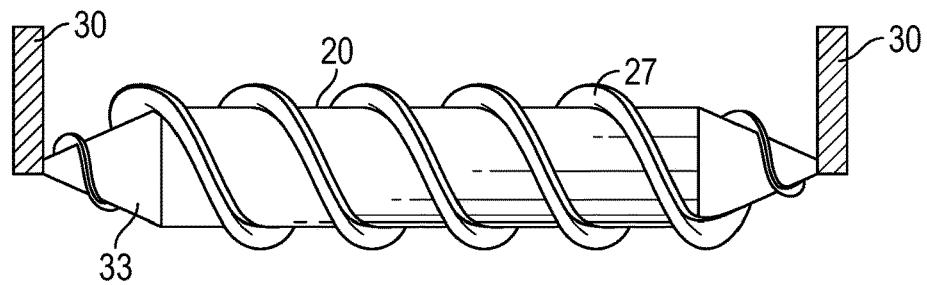
FIGS. 5*a*-5*c* show various locations of the drive unit relative to various cylinder designs.
Figure 5B:
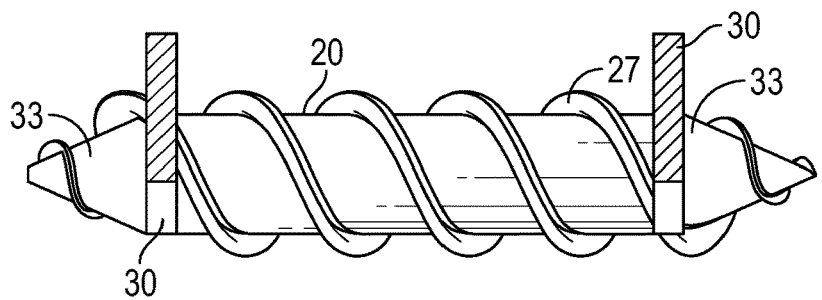
Figure 5C:
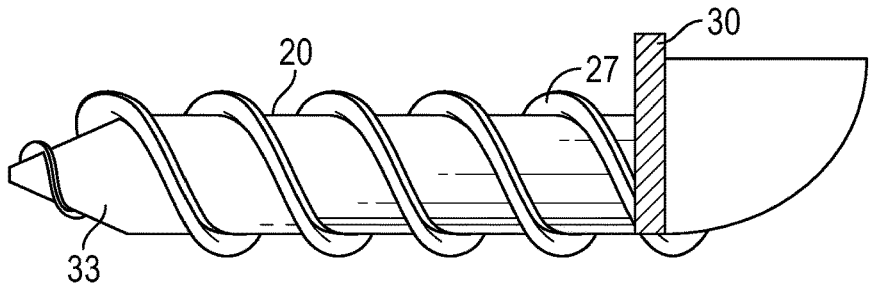

Three types of configurations with the drive units urging motion in the cylinders are described. With reference to FIG. 5a, the drive units 30 are positioned at each end of the cylinders 20 affixed to end caps 33, wherein the drive units 30 urge rotation of the cylinder by rotating the end caps 33 to which the cylinder is sealingly attached. With reference to FIG. 5b, the drive units 30 are positioned at either side of the cylinder 20, with immobile or driven end caps 33 at each end. The drive unit drives the cylinder and end caps directly. Threading on driven end caps is beneficial as it helps to break through material in the path of the rover, for example on this ice. In FIG. 5c, the cylinder 20 is driven from a single end by a drive unit 30, and the cylinder has a forward-facing end cap 33 affixed thereto. A bow hull is affixed to the other end to push material out of the path of the rover, aiding its progress through soft terrains.

Figure 6:
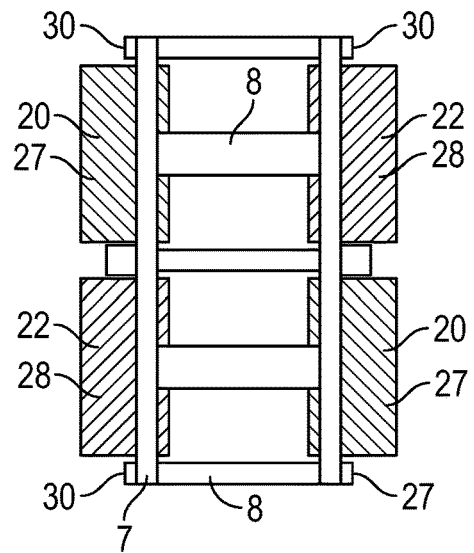
FIG. 6 is a top plan view of the quad-cylinder all-terrain rover, according to an embodiment of the present invention.

Another rover embodiment shown in FIG. 6 consists of a four-screw embodiment of the rover, having two cylinders 20, 22 on each side in an in-line configuration wherein each cylinder is independently driven such that it can still accomplish all motions described above. This embodiment has the distinct advantage of greater maneuverability on all ground and water types. Forward motion is accomplished by rotating cylinders 20 forwards and cylinders 22 in counter-rotation. Side rolling is accomplished by co-rotating all cylinders 20, 22. Rotation on the spot about the vehicle vertical center axis is accomplished by co-rotating the front cylinders 20, 22, and counter-rotating the rear cylinders 20, 22. Turns of various radius can be accomplished in either front screwing or side rolling motion by commanding a differential rotation speed between cylinder pairs. Each cylinder in this embodiment may have cone ends, tapered ends, or other advantageously shaped ends.

Figure 7:
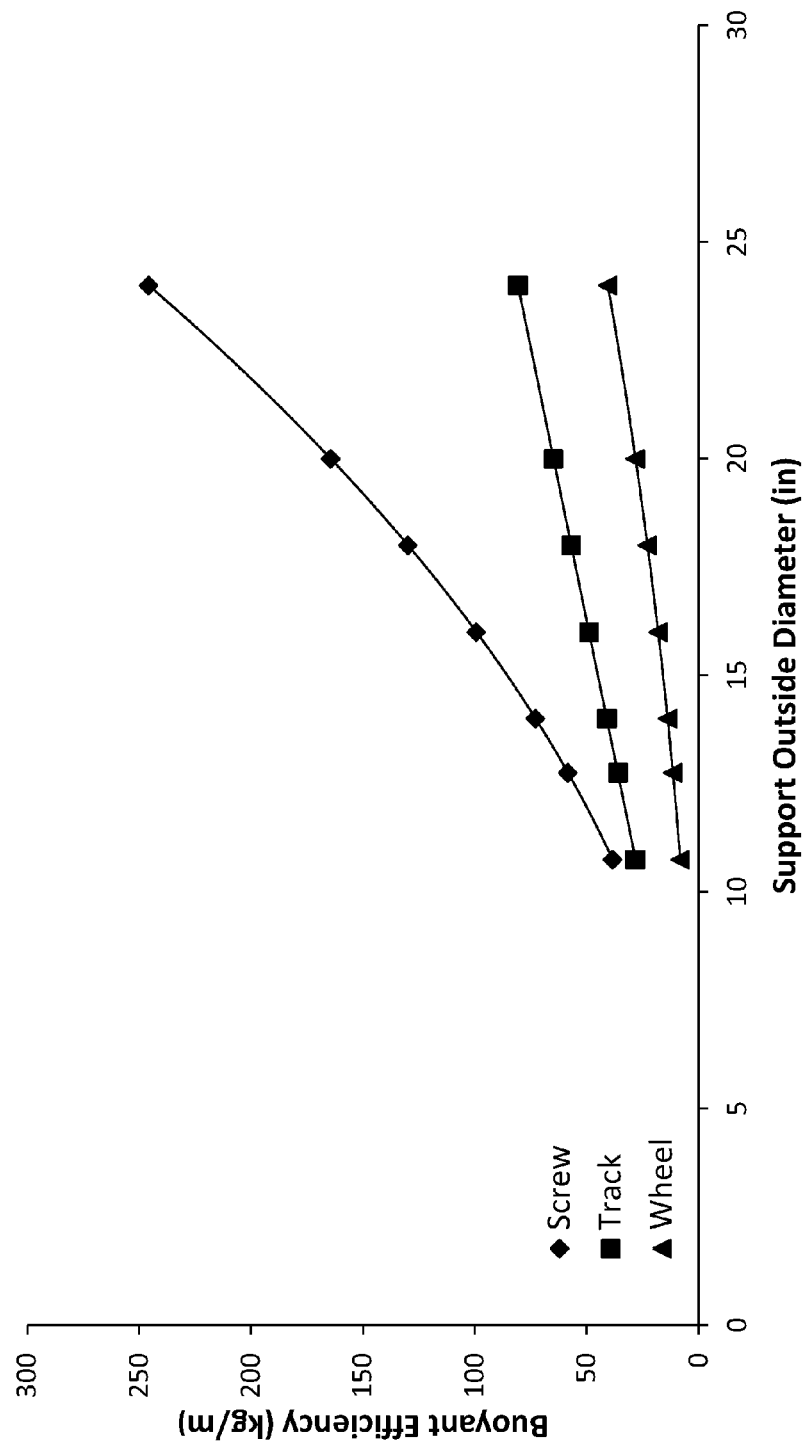
FIGS. 7 and 8 are charts showing buoyant efficiency and thread or flange angle comparison metrics, according to an embodiment of the present invention.
Figure 8:
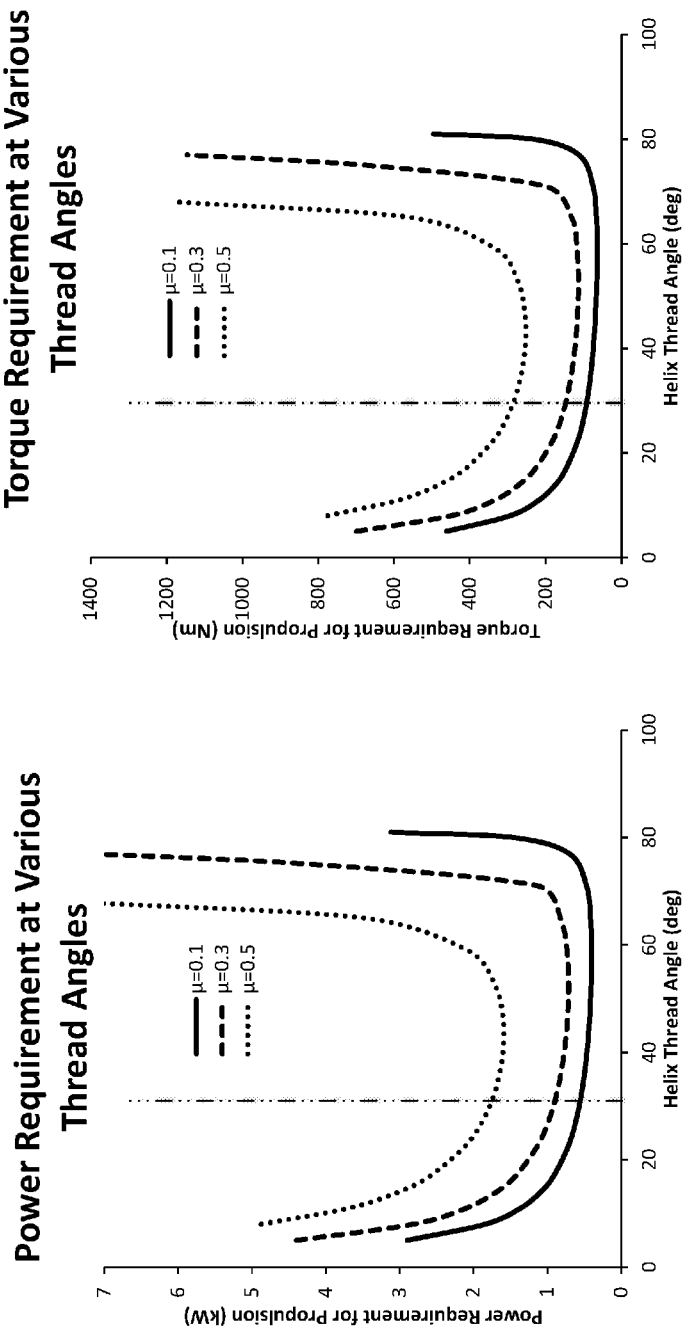

FIG. 7 is a chart showing buoyant efficiency comparison metrics for consideration in determining the mode of locomotion of an all-terrain rover. FIG. 8 shows considerations in selecting the helix angle for screw design.

In an embodiment, a valved core sampler is pushed into the surface to obtain a sample, and pulled out to retrieve the sample. The sampling equipment consists, in one embodiment, of a sampling shaft directed to push a soil core sampler into the surface below the rover at a specified location and retrieve sample before being raised within the rover again. In an embodiment, the soil core sampler comprises a cylinder with an auger tip with teeth for penetrating the ground and pushing a soil, sludge or sediment sample into the cylinder. As it is lowered, the tip of the stack rotates in order to cut into the surface to obtain the sample, wherein the sample passes by one or more valves for retention of soil core samples. The sampling stack then raises the soil core sampler containing the sample. In an embodiment other instruments may carried or towed by the rover to take measurements, for example an eddy covariance system, or hyperspectral imaging system. In an embodiment, sensors or sensor arrays may be deployed for remote in situ measurement, and then retrieved some time later.

In order to determine the undrained shear strength of clays, the sampler may also have a vane shear test tool comprising a shaft and a penetrating tip having one or more vanes of differing strength thereon, wherein the vane shear test tool is lowered into the surface and rotated at a prescribed speed while torque measurements are taken. The peak vane value is determined by a calibrated scale ring built into the tip assembly. Strain gauges or other sensors may also be used to collect data for the calculation of torque and shear strength. The meter may be lowered by the sampling stack into the surface below the rover.

In an embodiment, a cone penetrometer is pushed into the surface at a prescribed speed while force and other measurements are taken. In an embodiment, the test is performed by pushing a 1.41-inch diameter 55 to 60-degree cone through the underlying ground at a rate of 1 to 2 cm/sec. The test provides a ratio of tip and sleeve resistance, induced pore pressure, pore pressure ratio and lithologic interpretation of each 2 cm interval.

Other sampling tools that may be used with the rover are Cyre piston samplers, wireline fluid piston samplers, hand powered suction samplers, sonic thick-walled piston samplers, CRREL barrel samplers and grab samples, undisturbed surface samplers. Hyperspectral imagers, eddy covariance systems, and other sensors may also be carried or towed by the rover to collect various geotechnical measurements.

An excavator-like arm may be attached to the vehicle frame to provide another method to interact with and impart force to the surface, either for locomotion or sampling. In another embodiment a device similar to an outboard motor could be lowered into the surface when on a water or water-like terrain to provide additional propulsion.

A ruggedized and improved version of the rover contains improvements such as longer runtime due to larger batteries, replaceable batteries or an alternate fuel source, updated screw geometry to handle different ground types, ability to carry multiple sample tooling at once, ability to collect and carry multiple samples at once, updated control scheme and control interface. Ruggedization includes hardened and protected wiring, improved environmental sealing on electronics and drivetrain components to provide for waterproof electronics to prevent damage from rain or submersion of the rover, improved ease of servicing and adjusting mechanical components, more durable material selection and design for long life including long-life components.

With regards to screw geometry of the drive rollers, a more gentle flange angle relative to the axis of the roller increases the resistance to the motor and propels the vehicle further with a single revolution. This is preferable on low-resistance surfaces such as fluids and semi-fluids such as mud. A steeper flange angle provides less forward movement and less resistance per revolution of the rollers, and is preferable for firm surfaces. Useful flange helix angles are typically between approximately 20 and 65 degrees. FIGS. 5 and 6 show relative power requirements and torque requirements at select thread angles, wherein mu is the coefficient of friction between the ground and the screw. Work is ongoing to determine optimal screw geometry for various ground types of interest.

In an embodiment, the drive cylinders require a torque of 170 Nm and speed of 60 rpm, wherein the motors provide a peak torque of 240 Nm and an output speed of 54 rpm to each drive cylinder. 24V and 100 Ah batteries provide an estimated service life of 1.38 hours before recharging.

The invention has been described herein using specific embodiments for the purposes of illustration only. It will be readily apparent to one of ordinary skill in the art, however, that the principles of the invention can be embodied in other ways. Therefore, the invention should not be regarded as being limited in scope to the specific embodiments disclosed herein, but instead as being fully commensurate in scope with the following claims.

We claim:

1. An all-terrain rover, comprising:
 a. a ladder frame having one or more crosspieces;
 b. two drive units connected on opposite sides of the frame;
 c. first and second auger cylinders engaged with the drive units so as to be urged into rotation by the drive units, each cylinder comprising:
 d. a sealed hollow cylinder; and
 e. a spiral auger flange affixed to the exterior of the cylinder,
wherein the drive units are in contact with axes of the auger cylinders and the flange of the first cylinder is wound in an opposite direction to the flange of the second cylinder, and wherein the cylinders are each counter-rotated to urge the rover forward, and wherein sampling equipment is mounted onto the rover, and wherein the sampling eqipment comprising a valved core sampler tip connected to a descent mechanism to lower the tip into a surface below the rover.

2. The all-terrain rover of claim 1 wherein each cylinder further comprises a conical end cap at each end.

3. The all-terrain rover of claim 1 wherein each cylinder further comprises a frustaconical end cap at each end.

4. The all-terrain rover of claim 1 wherein each cylinder is buoyant.

5. The all-terrain rover of claim 1 wherein each cylinder is coated with a hydrophobic coating.

6. The all-terrain rover of claim 1 where each cylinder is rotated in the same direction to urge the rover in a sideways direction.

7. The all-terrain rover of claim 1 wherein only one cylinder is rotatable to produce a skid turn.

8. The all-terrain rover of claim 1 further comprising a control unit connected to each of the drive units to control a rotation speed and direction of the drive units.

9. The all-terrain rover of claim 1 wherein the rover may be controlled in a remote-controlled configuration or in a robotic configuration.

10. The all-terrain rover of claim 1 further comprising third and fourth cylinders, wherein the third cylinder is adjacent and coaxial to the first cylinder, and the fourth cylinder is adjacent and coaxial to the second cylinder.

11. The all-terrain rover of claim 1 further comprising a platform across the frame.

12. An all-terrain rover comprising:
 a. a ladder frame having one or more crosspieces;
 b. two drive units connected on opposite sides of the frame;
 c. first and second auger cylinders engaged with the drive units so as to be urged into rotation by the drive units, each cylinder comprising:
 d. a sealed hollow cylinder; and e. a spiral auger flange affixed to the exterior of the cylinder, wherein the drive units are in contact with the axes of the auger cylinders, and the axes of the auger cylinders are parallel to one another, and the flange of the first cylinder is wound in an opposite direction to the flange of the second cylinder, and wherein the cylinders are each counter-rotated to urge the rover forward, and wherein sampling equipment is mounted onto the rover, and wherein the sampling equipment comprises a cone penetrometer connected to a descent mechanism to lower the tip into a surface below the rover.

13. The all-terrain rover of claim 1, further comprising an excavator arm attached to the frame.

14. An all-terrain rover, comprising:
   a. a ladder frame having one or more crosspieces, the frame having first and second sides;
   b. first and second auger cylinders positioned coaxially, rotatably mounted on the first side, each cylinder comprising:
      a sealed hollow cylinder; and
      a spiral auger flange affixed to the exterior of the cylinder,
   c. third and fourth auger cylinders positioned coaxially, rotatably mounted on the second side, each cylinder comprising:
      a sealed hollow cylinder; and
      a spiral auger flange affixed to the exterior of the cylinder, and
   d. at least one drive unit on each side, each drive unit engaged with at least one auger cylinder on that side so as to urge the rotation of the cylinder;

wherein the axes of the first and second auger cylinders are parallel with axes of the third and fourth auger cylinders, and the flanges of the first and second cylinders are wound in an opposite direction to the flanges of the third and fourth cylinders, and wherein the first and second cylinders are counter-rotated relative to the third and fourth cylinders to urge motion in the rover, and wherein sampling equipment is mounted onto the rover, and wherein the sampling equipment comprises a valved core sampler tip connected to a descent mechanism to lower the tip into a surface below the rover.

15. The all-terrain rover of claim 14 wherein each cylinder further comprises a conical end cap at each end.

16. The all-terrain rover of claim 14 wherein each cylinder is sealed and buoyant.

* * * * *